US012672622B2

(12) United States Patent
Kaij et al.

(10) Patent No.: US 12,672,622 B2
(45) Date of Patent: Jul. 7, 2026

(54) STAY GREEN CUCURBITACEAE PLANT

(71) Applicant: Enza Zaden Beheer B.V., Enkhuizen (NL)

(72) Inventors: Bart Kaij, Enkhuizen (NL); Yusuf Sen, Enkhuizen (NL); Wilhelmina Antonia Cornelia Anna Leijten, Enkhuizen (NL); Laura Naranjo Peña, Enkhuizen (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 182 days.

(21) Appl. No.: 18/285,048

(22) PCT Filed: Apr. 1, 2021

(86) PCT No.: PCT/EP2021/058684
§ 371 (c)(1),
(2) Date: Sep. 29, 2023

(87) PCT Pub. No.: WO2022/207114
PCT Pub. Date: Oct. 6, 2022

(65) Prior Publication Data
US 2024/0180095 A1      Jun. 6, 2024

(51) Int. Cl.
| | |
|---|---|
| *A01H 6/34* | (2018.01) |
| *A01H 1/00* | (2006.01) |
| *A01H 1/06* | (2006.01) |
| *A01H 5/08* | (2018.01) |
| *C07K 14/415* | (2006.01) |

(52) U.S. Cl.
CPC .................. *A01H 6/34* (2018.05); *A01H 1/06* (2013.01); *A01H 1/1205* (2021.01); *A01H 5/08* (2013.01); *C07K 14/415* (2013.01)

(58) Field of Classification Search
None
See application file for complete search history.

(56) References Cited

FOREIGN PATENT DOCUMENTS

| | | | |
|---|---|---|---|
| WO | WO-2007/042070 A1 | 4/2007 | |
| WO | WO-2011/144672 A1 | 11/2011 | |
| WO | WO-2014/140026 A1 | 9/2014 | |
| WO | WO-2015/024119 A1 | 2/2015 | |
| WO | WO-2016012346 A1 * | 1/2016 | ............. A01H 6/346 |

OTHER PUBLICATIONS

Bade et al., "Genome-wide identification and analysis of the SGR gene family in *Cucumis melo* L.", Genet Mol Res 17: 15 (2016).
International Search Report and Written Opinion for International Application No. PCT/EP2021/058684 dated Dec. 10, 2021.
Barry et al. (2008) "Amino acid substitutions in homologs of the Stay-Green protein are responsible for the green-flesh and chlorophyll retainer mutations of tomato and pepper"—Plant Physiol. 147(1): 179-87.
Blast analysis submitted by Opponent in Opposition Proceedings for EP Application No. 15738904.0 on Jun. 2, 2025.
Call et al. (2012) "Screening Cucumber for Resistance to Downy Mildew Caused by Pseudoperonospora cubensis (Berk. and Curt.) Rostov."—Crop Science, vol. 52, p577 - 592.
Experimental data submitted by Opponent in Opposition Proceedings for EP Application No. 15738904.0 on Jun. 2, 2025.
Genome assembly Cucumber (GY14) v1 genome release submitted by Opponent in Opposition Proceedings for EP Application No. 15738904.0 on Jun. 2, 2025.
Notice of Opposition filed in EP Application No. 15738904.0 dated Jun. 2, 2025, 19 pages.
Park et al. (2007) "The Senescence-Induced Staygreen Protein Regulates Chlorophyll Degradation"—The Plant Cell, vol. 19: 1649-1664.
Wang et al. "Staygreen, Stay healthy: a loss-of-susceptibility mutation in the Staygreen gene provides durable, broad-spectrum disease resistances for over 50 years of US cucumber production", New Phytologist (2019) 221: 415-430 and supporting information.
Wang et al., Yuhui, "Staygreen, Stay Healthy: a loss-of-susceptibility mutation in the Staygreen gene provides durable, broad-spectrum disease resistances for over 50 years of US cucumber production", New Phytologist, Jun. 13, 2018.
Yang et al. (2012) "Chromosome rearrangements during domestication of cucumber as revealed by high-density genetic mapping and draft genome assembly", The Plant Journal 71: 895-906.

* cited by examiner

*Primary Examiner* — Cathy Kingdon
(74) *Attorney, Agent, or Firm* — Foley Hoag LLP; Brendan T. Jones

(57) ABSTRACT

The present invention relates to a Cucurbitaceae plant which provides fruits having an improved shelf life. Further, the present invention relates to seeds, plant tissue, fruits or plants parts of a Cucurbitaceae plant. Further aspect of the present invention relates to a method for providing a Cucurbitaceae plant which provides fruits with an improved shelf life. According to yet another aspect the present invention relates to nucleic acids and amino acids related to the present improved shelf life trait.

8 Claims, 4 Drawing Sheets

Figure 1:
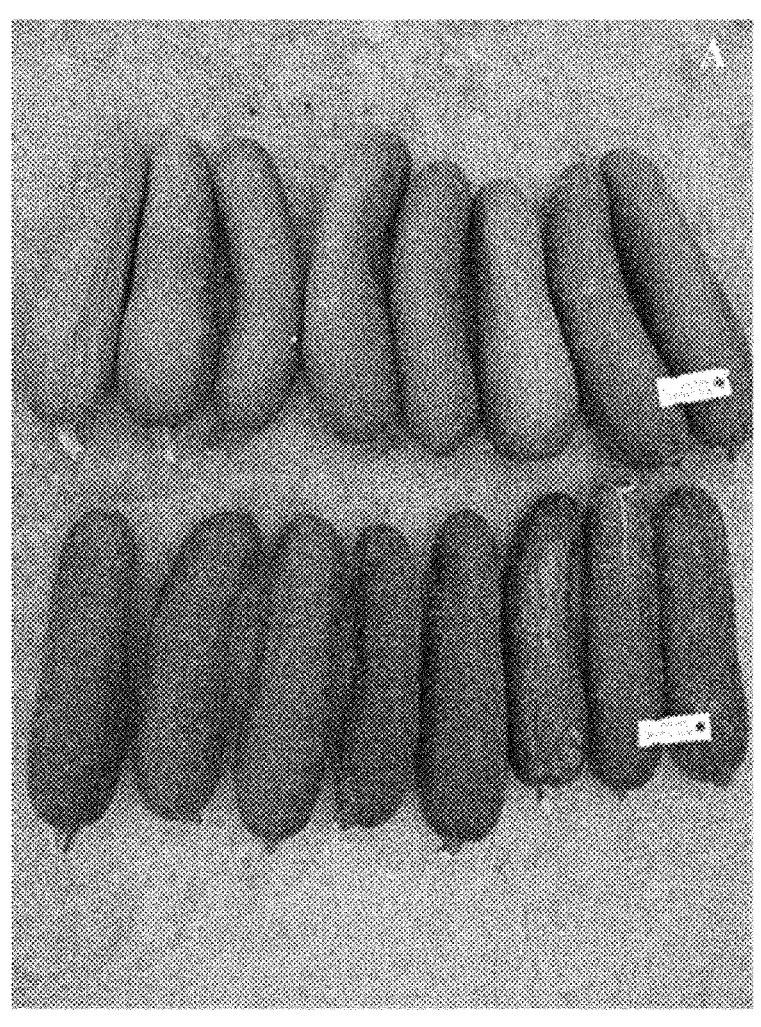
Figure 1:
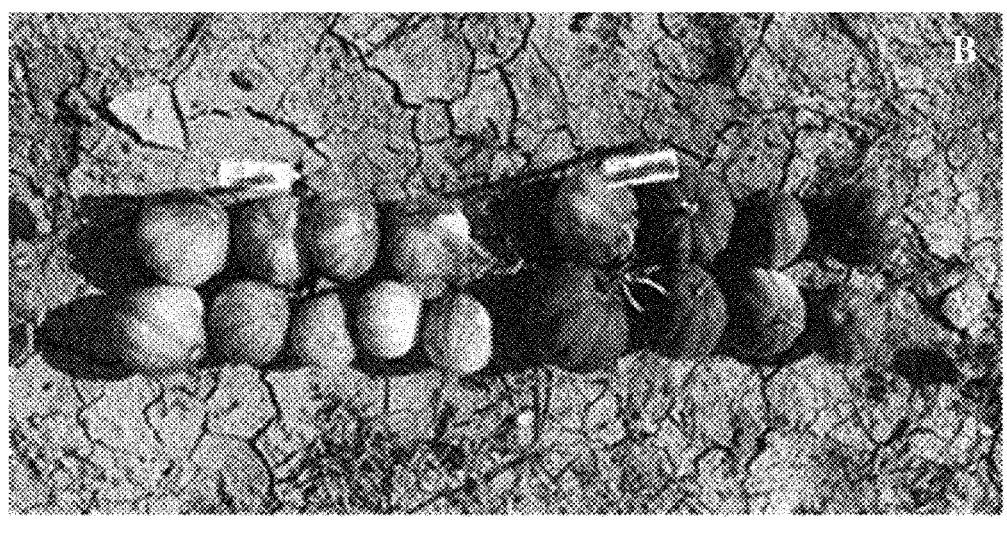

Specification includes a Sequence Listing.

FIGURE 4

```
                                         1        10        20        30        40        50        60
                                         |        |         |         |         |         |         |
          Cucurbita pepo SGR Protein     MRGLTANSSVLLAP-SNPYQ-NSSLFPSKRKSKKKNHAMVPVARLFGPAIFEASKLKVLF
   Cucurbita pepo Mutant SGR Protein     MRGLTANSSVLLAP-SNPYQ-NSSLFPSKRKSKKKNHAMVPVARLFGPAIFEAFKLKVLF
             Cucumis melo SGR Protein    MRVLTSNSSPLLVPSSNPYQDSSSLFLCKRKSKEKNHRMVPMARLFGPAIFEASKLKVLF
      Cucumis melo Mutant SGR Protein    MRVLTSNSSPLLVPSSNPYQDSSSLFLCKRKSKEKNHRMVPMARLFGPAIFEASKLKVLF
        Citrullus lanatus SGR Protein    MRVLTTNSSVLLVP-SNPYQ-NSSLFPCKRKSKKNNHAIVPMARLFGPAIFEASKLKVLF
    Cucurbita argyrosperma SGR Protein   MRGLTANSSVLLAP-SNPYQ-NSSLFPSKRKSKKKNHAMVPVARLFGPAIFEASKLKVLF
         Cucurbita maxima SGR Protein    MRGLTANSSVLLAP-SNPYQ-SSSLFPSKRKSKKKNHAMVPVARLFGPAIFEASKLKVLF
       Cucurbita moschata SGR Protein    MRGLTANSSVLLAP-SNPYQ-NSSLFPSKRKSKKKNHAMVPVARLFGPAIFEASKLKVLF
       Lagenaria siceraria SGR Protein   MRVLTTNSSVLLVP-SNPYQ-NSSFFPCKRKSKKNNHAIVPVARLFGPAIFEASKLKVLF Cucurbita pepo SGR Protein     LGVDEKKHPGKFPRTYTLTHSDITSKLTLAISQTINNSQLQGWYNWLQRDEVVGEWKKVK
   Cucurbita pepo Mutant SGR Protein     LGVDEKKHPGKFPRTYTLTHSDITSKLTLAISQTINNSQLQGWYNWLQRDEVVGEWKKVK
             Cucumis melo SGR Protein    LGVDEKKHPGKFPRTYTLTHSDITSKLTLAISQSINNSQLQGWYNWLQRDEVVAEWKKVQ
      Cucumis melo Mutant SGR Protein    LGVDEKKHPGKFPKTYTLTHSDITSKLTLAISQSINNSQLQGWYNWLQRDEVVAEWKKVQ
        Citrullus lanatus SGR Protein    LGVDEKKHPGKFPRTYTLTHSDITSKLTLAISQSINNSQLQGWYNWLQRDEVVGEWKKVK
    Cucurbita argyrosperma SGR Protein   LGVDEKKHPGKFPRTYTLTHSDITSKLTLAISQTINNSQLQGWYNWLQRDEVVGEWKKVK|
         Cucurbita maxima SGR Protein    LGVDEKKHPGKFPRTYTLTHSDITSKLTLAISQTINNSQLQGWYNWLQRDEVVGEWKKVK
       Cucurbita moschata SGR Protein    LGVDEKKHPGKFPRTYTLTHSDITSKLTLAISQTINNSQLQGWYNWLQRDEVVGEWKKVK
       Lagenaria siceraria SGR Protein   LGVDEKKHPGKFPRTYTLTHSDITSKLTLAISQSINNSQLQGWYNWLQRDEVVGEWKKVK Cucurbita pepo SGR Protein     GKMSLHVHCHISGGHFLLDLCANLRYFIFRKELPVVLNAFVHGDVDLFNNYPELQDALVW
   Cucurbita pepo Mutant SGR Protein     GKMSLHVHCHISGGHFLLDLCANLRYFIFRKELPVVLNAFVHGDVDLFNNYPELQDALVW
             Cucumis melo SGR Protein    GKMSLHVHCHISGGHFLLDLCANLRYFIFRRELPVVLNAFVHGDVDLFKNYPELQEAMVW
      Cucumis melo Mutant SGR Protein    GKMSLHVHCHISGGHFLLDLCANLRYFIFRRELPVVLNAFVHGDVDLFKNYPELQEAMVW
        Citrullus lanatus SGR Protein    GKMSLHVHCHISGGHFLLDLCAKLRYFIFRKELPVVLNAFVHGDVDLFNNYPELQEALVW
    Cucurbita argyrosperma SGR Protein   GKMSLHVHCHISGGHFLLDLCANLRYFIFRKELPVVLNAFVHGDVDLFNNYPELQDALVW
         Cucurbita maxima SGR Protein    GKMSLHVHCHISGGHFLLDLCANLRYFIFRKELPVVLNAFVHGDVDLFNNYPELQDALVW
       Cucurbita moschata SGR Protein    GKMSLHVHCHISGGHFLLDLCANLRYFIFRKELPVVLNAFVHGDVDLFNNYPELQDALVW
       Lagenaria siceraria SGR Protein   GKMSLHVHCHISGGHFLLDLCANLRYFIFRKELPVVLNAFVHGDVDLFNNYPELQEALVW Cucurbita pepo SGR Protein     VYFHSKIPEFNKVECWGPLKNPAPPSAGLDG-SNSDE-----PIWDMGQMERPKPCQEDC
   Cucurbita pepo Mutant SGR Protein     VYFHSKIPEFNKVECWGPLKNPAPPSAGLDG-SNSDE-----PIWDMGQMERPKPCQEDC
             Cucumis melo SGR Protein    VYFHSKIPEFNKVECWGPLKDPAPPSSGLDGRPKSDE-----PMWELSRMERPKPCQEDC
      Cucumis melo Mutant SGR Protein    VYFHSKIPEFNKVECWGPLKDPAPPSSGLDGRPKSDE-----PMWELSRMERPKPCQEDC
        Citrullus lanatus SGR Protein    VYFHSNIPEFNKVECWGPLKDPAPPSTGPYG-PKSDEPTQSQSMWDLGRLERPKPCQEDC
    Cucurbita argyrosperma SGR Protein   VYFHSKIPEFNKVECWGPLKDPAPPSAGLDG-SNSDE-----PIWDMGQMERPKPCQEDC
         Cucurbita maxima SGR Protein    VYFHSKIPEFNKVECWGPLKDPAPPSAGLDG-SNSDG-----SIWDMGQMERPKPCQEDC
       Cucurbita moschata SGR Protein    VYFHSKIPEFNKVECWGPLKDPAPPSAGLDG-SNSDE-----PIWDMGQMERPKPCQEDC
       Lagenaria siceraria SGR Protein   VYFHSKIPEFNKVECWGPIKDPAPPSTG----PKSDEGTQSQPMWDLGRLERPKPCQEDC Cucurbita pepo SGR Protein     SCCFPTIPSISWSPKN-ELEST
   Cucurbita pepo Mutant SGR Protein     SCCFPTIPSISWSPKN-ELEST
             Cucumis melo SGR Protein    NCCFPTIPSISWSPKNSELEST
      Cucumis melo Mutant SGR Protein    NCCFPTIPSISWSPKNSELEST
        Citrullus lanatus SGR Protein    NCCFPTIPSISWSPQN-ELEST
    Cucurbita argyrosperma SGR Protein   SCCFPTIPSISWSPKN-ELEST
         Cucurbita maxima SGR Protein    SCCFPTIPSISWSPKN-ELEST
       Cucurbita moschata SGR Protein    SCCFPTIPSISWSPKN-ELEST
       Lagenaria siceraria SGR Protein   NCCFPTIPSISWSPKN-ELEST
```

STAY GREEN CUCURBITACEAE PLANT

RELATED APPLICATIONS

This application is a U.S. National Phase of International Patent Application No. PCT/EP2021/058684, filed Apr. 1, 2021, which is hereby incorporated by reference in its entirety.

The present invention relates to a Cucurbitaceae plant which provides fruits having an improved shelf life. Further, the present invention relates to seeds, plant tissue, fruits or plants parts of a Cucurbitaceae plant. Further aspect of the present invention relates to a method for providing a Cucurbitaceae plant which provides fruits with an improved shelf life. According to yet another aspect the present invention relates to nucleic acids and amino acids related to the present improved shelf life trait.

Cucurbitaceae plants, including squash, pumpkin, cucumber and melon are already cultivated for at least 3.000 years and several different cultivars have emerged, which are grown and market on the global market. The Cucurbitaceae fruits are mainly eaten in the unripe green form since the ripe yellow form normally becomes bitter and sour. Accordingly, the Cucurbitaceae fruits, such as squash and cucumber, are commonly harvested while still green and are generally used for both the pickling industry and the fresh market, which latter usage has the greatest added value for the farmers. Due to its relatively short shelf life, storage and shipping of fresh Cucurbitaceae fruits is, however, difficult and expensive. Cooling, which is generally used to extend the shelf life of fresh products, cannot be applied for Cucurbitaceae fruits as these fruits are not suitable for storage at low temperatures due to chill injury.

It is known to extend the shelf life of Cucurbitaceae fruits by for example wrapping them in sealing foil or storing them under controlled conditions (>10° C.). However, additional processing steps or specific storage measures thus have to be taken. In addition, in this way the shelf life is extended only in the specific Cucurbitaceae that have been wrapped in foil, or have been stored under said specific conditions. Further, although the shelf life is extended by wrapping Cucurbitaceae in foil, these wrapped Cucurbitaceae turn yellow within a time period of about two weeks.

Furthermore, under stress conditions (i.e. drought, disease), Cucurbitaceae plant senescence start very early and leaves become yellow which negatively affects plants health and crop yield. Therefore, it would be of importance to find a solution to inhibit this natural process given the advantage in the field in terms of plant continuation, crop yield and harvest period extension.

Given the above, there is a need in the art for Cucurbitaceae plants providing fruits having an extended shelf life and wherein the process of yellowing of the leaves of the plants is inhibited or reduced.

Therefore, it is an object of the invention, amongst other objects, to provide Cucurbitaceae plants providing fruits having an extend shelf life and wherein the plant and fruits are more resistant to yellowing.

This object, amongst other objects, is met by providing a Cucurbitaceae plant according to the appended claims.

Specifically, this object, amongst other objects, is met by a Cucurbitaceae plant which provides fruits having an improved shelf life, wherein said plant comprises a mutated stay green gene, wherein said stay green gene encodes for a protein having at least 87% sequence identity with SEQ ID No. 2 of SEQ ID 6, and wherein the mutated stay green gene comprises at least one mutation in the stay green gene resulting in an amino acid substitution of Serine(S) to Phenylalanine (F) or Leucine (L) at amino acid position 52 or position 54 (S52F, S52L, S54F or S54L), and/or an amino acid substitution of Arginine (R) to Lysine (K) at amino acid position 72 or position 74 (R72K or R74K) in the protein sequence represented by SEQ ID No. 2 or SEQ ID No. 6, respectively. Preferably the Cucurbitaceae plant of present invention comprises a mutated stay green gene that encodes for a protein comprising the amino acid sequence as shown in SEQ ID NO. 2 or SEQ ID No. 6, or amino acid sequences with more than 90% identity, such as more than 91%, 92% or 93%, preferably more than 94% identity such as more than 95%, more preferably more than 96% identity such as more than 97%, even more preferably more than 98% identity or more than 99% identity with SEQ ID NO. 2 or SEQ ID No. 6. The expression of said mutated stay green gene is reduced as compared to the expression of a "wild type" stay green gene not comprising the specific mutation, in a Cucurbitaceae plant not providing fruits having an improved shelf life, or the enzymatic activity of said protein is reduced as compared to the enzymatic activity of said protein in a Cucurbitaceae plant not providing fruits having an improved shelf life. The mutated protein comprising the S52F mutation, as shown in SEQ ID NO. 4, or R74K mutation, as shown in SEQ ID NO. 20, is highly correlated with the improved shelf life trait of the present invention and a stay green phenotype of the plant and its fruit, since an improved shelf life of at least 4 to 5 weeks is observed for fruits from a Cucurbitaceae plant comprising a mutated stay green gene encoding the present protein.

In the present invention, the identified gene encodes for a chloroplast protein and is required for the initiation of chlorophyll breakdown in plants. Modifying this gene function inhibits chlorophyll breakdown and provides a delay in senescence in the field. A mutation was induced using EMS technology providing a mutation in the stay green (SGR) gene in C. pepo and C. melo. It was surprisingly found that an amino acid change at position 52 or 54 from a serine to a phenylalanine or leucine and/or an amino acid change at position 72 or 74 from a arginine to a lysine related to an improved delay of senescence and delay maturity in plant and fruits as compared to other mutations in the stay green gene. Other mutations did not result in the stay green phenotype, such as M1I, A13V, P25S, S30F, G45R, P170L, P188S, P205L, E221K and E251K, as determined in C. pepo and C. melo.

With improved shelf life, as used in the present context, is meant an improved storability of harvested unripe green Cucurbitaceae, which Cucurbitaceae stay green for longer periods of time than comparable standard harvested unripe green Cucurbitaceae. Preferably, the present Cucurbitaceae stay green for a time period up to 4 or 5 weeks. Plants of the invention can be distinguished from prior art plants by measuring the time period under standard storage conditions (about 12° C.) that the Cucurbitaceae fruits stay green. Conventional Cucurbitaceae fruits turn yellow within 1 or 2 weeks; whereas Cucurbitaceae fruits according to the present invention turn yellow after a time period of at least 4 or at least 5 weeks. In addition under stress conditions (i.e. drought, disease), Cucurbitaceae plant senescence is delayed resulting in that leaves maintain their green phenotype for longer periods which positively affects plants health and crop yield. Further, stay green gene expression levels in the present plants and the reference plants can be determined using any suitable and generally known Molecular Biology technique such as a quantitative Polymerase Chain Reaction (PCR) or mRNA hybridization.

According to the present invention, an enzymatic activity is reduced in comparison with the activity of the present protein in a Cucurbitaceae plant which does not provide Cucurbitaceae fruits having an extended shelf life. The term 'not providing Cucurbitaceae plants having an extended shelf life' indicates a shelf life, determined in an phenotypic test and appropriate reference plant, such as a parent plant, being less than the shelf life than observed for Cucurbitaceae fruits of the present invention. Suitable reference plants can, besides parent plants, also be plants generally designated as providing marketable Cucurbitaceae fruits.

The present protein has a chlorophyll decarboxylase function wherein, amongst other reactions, a carboxyl group is removed and carbon dioxide is released. Accordingly, the present reduced activity can be determined using an assay measuring compounds being either the starting compounds or the resulting compounds of the enzymatic reaction. As a suitable alternative, protein levels, being inherently indicative of a reduced activity, of the present proteins can be determined by, for example, ELISA or protein hybridization both being techniques commonly known to the skilled person.

The present Cucurbitaceae plants can be obtained by mutagenesis of Cucurbitaceae plants. For example, mutations, either at the expression level or the protein level, can be introduced in these plants by using mutagenic chemicals such as ethyl methane sulfonate (EMS) or by irradiation of plant material with gamma rays or fast neutrons. Mutagenized plants carrying mutations in the present gene can be readily identified by using the TILLING (Targeting Induced Local Lesions IN Genomes) method (McCallum et al. (2000) Targeted screening for induced mutations. Nat. Biotechnol. 18, 455-457, and Henikoff et al. (2004) TILLING. Traditional mutagenesis meets functional genomics. Plant Physiol. 135, 630-636). Briefly, this method is based on the PCR amplification of a gene of interest from genomic DNA of a large collection of mutagenized plants in the M2 generation. By DNA sequencing or by scanning for point mutations using a single-strand specific nuclease, such as the CEL-I nuclease (Till et al. (2004) Mismatch cleavage by single-strand specific nucleases. Nucleic Acids Res. 32, 2632-2641) individual plants having a mutation in the present genes are identified.

According to a preferred embodiment of the present invention the present plants detailed above are not plants exclusively obtained by means of an essentially biological process.

According to a preferred embodiment, the present invention relates to the Cucurbitaceae plant, wherein said plant is one or more selected from the group consisting of *Cucurbita pepo* (Squash), *Cucurbita moschata* (Pumpkin), *Cucurbita maxima* (Pumpkin), *Cucurbita argyrosperma* (Silver-seed Gourd), *Lagenaria siceraria* (Bottle gourd), *Citrullus lanatus* (Watermelon), and *Cucumis melo* (Melon), preferably *Cucurbita pepo* and/or *Cucumis melo*.

According to another preferred embodiment, the present invention relates to the Cucurbitaceae plant, wherein said plant is one or more selected from the group consisting of;

*Cucurbita pepo* wherein said mutated stay green gene encodes for a protein sequence of SEQ ID No. 2 that comprises an amino acid substitution of Serine to Phenylalanine (S52F) at position 52, and/or an amino acid substitution of Arginine (R) to Lysine (K) at position 72 (R72K), corresponding with a nucleotide mutation of C to T at position 155 (C155T) and/or a nucleotide mutation of G to A at position 215 (G215A) in the coding sequence represented by SEQ ID No. 1 and/or

*Cucumis melo* wherein said mutated stay green gene encodes for a protein sequence of SEQ ID No. 6 that comprises an amino acid substitution of Serine to Leucine (S54L) at position 54, and/or an amino acid substitution of Arginine (R) to Lysine (K) at position 74 (R74K), corresponding with a nucleotide mutation of C to T at position 161 (C161T) and/or a nucleotide mutation of G to A at position 221 (G221A) in the coding sequence represented by SEQ ID No. 5, and/or

*Cucurbita moschata* wherein said mutated stay green gene encodes for a protein sequence of SEQ ID No. 12 that comprises an amino acid substitution of Serine to Phenylalanine (S52F) at position 52, and/or an amino acid substitution of Arginine (R) to Lysine (K) at position 72 (R72K), corresponding with a nucleotide mutation of C to T at position 155 (C155T) and/or a nucleotide mutation of G to A at position 215 (G215A) in the coding sequence represented by SEQ ID No. 11, and/or

*Cucurbita maxima* wherein said mutated stay green gene encodes for a protein sequence of SEQ ID No. 10 that comprises an amino acid substitution of Serine to Phenylalanine (S52F) at position 52, and/or an amino acid substitution of Arginine (R) to Lysine (K) at position 72 (R72K), corresponding with a nucleotide mutation of C to T at position 155 (C155T) and/or a nucleotide mutation of G to A at position 215 (G215A) in the coding sequence represented by SEQ ID No. 9, and/or

*Cucurbita argyrosperma* wherein said mutated stay green gene encodes for a protein sequence of SEQ ID No. 8 that comprises an amino acid substitution of Serine to Phenylalanine (S52F) at position 52, and/or an amino acid substitution of Arginine (R) to Lysine (K) at position 72 (R72K), corresponding with a nucleotide mutation of C to T at position 155 (C155T) and/or a nucleotide mutation of G to A at position 215 (G215A) in the coding sequence represented by SEQ ID No. 7, and/or

*Lagenaria siceraria* wherein said mutated stay green gene encodes for a protein sequence of SEQ ID No. 14 that comprises an amino acid substitution of Serine to Leucine (S52L) at position 52, and/or an amino acid substitution of Arginine (R) to Lysine (K) at position 72 (R72K), corresponding with a nucleotide mutation of C to T at position 155 (C155T) and/or a nucleotide mutation of G to A at position 215 (G215A) in the coding sequence represented by SEQ ID No. 13, and/or

*Citrullus lanatus* wherein said mutated stay green gene encodes for a protein sequence of SEQ ID No. 16 that comprises an amino acid substitution of Serine to Leucine (S52L) at position 52, and/or an amino acid substitution of Arginine (R) to Lysine (K) at position 72 (R72K), corresponding with a nucleotide mutation of C to T at position 155 (C155T) and/or a nucleotide mutation of G to A at position 215 (G215A) in the coding sequence represented by SEQ ID No. 15, and/or The sequence homology among stay green proteins of various Cucurbitaceae plants were analyzed using multiple alignment software and showed that that the SGR proteins share a sequence homology of at least 87%, and preferably at least 90% sequence identity between Cucurbitaceae plants (See also Table 1).

According to a preferred embodiment the present invention relates to the Cucurbitaceae plant, wherein said plant is a *C. pepo* or *C. melo* and the mutated stay green gene encodes a protein comprising an amino acid sequence as shown in SEQ ID NO. 4 or SEQ ID NO. 18, respectively.

According to yet a further preferred embodiment, the present stay green gene is present in homozygous form, thereby providing an improved shelf life of the Cucurbitaceae fruits.

According to yet another preferred embodiment, the present invention relates to the Cucurbitaceae plant, wherein said mutated stay green gene is obtainable from the deposit made in the National Collection of Industrial, Food and Marine Bacteria (NCIMB) under deposit number NCIMB 43480 or NCIMB 43513. Seeds of *C. pepo* and *C. melo* of present invention are deposited at NCIMB Ltd, Ferguson Building, Craibstone Estate, Bucksburn, Aberdeen AB21 9YA, Scotland, under the number NCIMB 43480 (6 Sep. 2019) and NCIMB 43513 (12 Nov. 2019), respectively.

According to a second aspect, the present invention relates seeds, plant tissue, fruits or plants parts of a Cucurbitaceae plant of present invention comprising a mutated stay green gene providing an improved fruit shelf life. Preferably the stay green gene encodes an amino acid sequence having more than 90% identity, preferably more than 94% identity, more preferably more than 96% identity, even more preferably more than 98% identity with SEQ ID NO. 4 or SEQ ID NO. 18.

According to a further aspect, the present invention relates to a method for providing a Cucurbitaceae plant of present invention, wherein the method comprises the step of providing a Cucurbitaceae plant comprising a mutated stay green gene, wherein said stay green gene encodes for a protein having at least 87% sequence identity with SEQ ID No. 2 of SEQ ID 6, and wherein the mutated stay green gene comprises at least one mutation in the stay green gene resulting in an amino acid substitution of Serine (S) to Phenylalanine (F) or Leucine (L) at amino acid position 52 or position 54 (S52F, S52L, S54F or S54L), and/or an amino acid substitution of Arginine (R) to Lysine (K) at amino acid position 72 or position 74 (R72K or R74K) in the protein sequence represented by SEQ ID No. 2 or SEQ ID No. 6, respectively.

According to a further aspect, the present invention relates to a method for obtaining a Cucurbitaceae plant of present invention which provides fruits having an improved shelf life, wherein the method comprises the steps of, a) crossing a Cucurbitaceae plant comprised of a mutated stay green gene with a Cucurbitaceae plant that does not comprise said mutated stay green gene, b) optionally, selfing the plant obtained in step a) for at least one time, c) selecting the plants that comprise said stay green gene or nucleic acid sequence.

According to a preferred embodiment, the present invention relates to the method for obtaining a Cucurbitaceae plant, wherein the method comprises the step of providing at least one mutation in the stay green gene resulting in an amino acid substitution of Serine (S) to Phenylalanine (F) or Leucine (L) at amino acid position 52 or position 54 (S52F, S52L, S54F or S54L), and/or an amino acid substitution of Arginine (R) to Lysine (K) at amino acid position 72 or position 74 (R72K or R74K) in the protein sequence represented by SEQ ID No. 2 or SEQ ID No. 6, respectively.

According to another preferred embodiment, the present invention relates to the method for obtaining and providing a Cucurbitaceae plant, wherein the mutation in the stay green gene is obtained by gene editing techniques, preferably by mutagenesis and/or CRISPR/Cas. Preferably the mutation in the stay green gene is a non-natural mutation.

According to a further aspect, the present invention relates to a protein for providing Cucurbitaceae plants which provides fruits with an improved shelf life, wherein the protein comprises SEQ ID No. 4 or SEQ ID No. 18 or having at least 87% sequence identity with SEQ ID No. 4 and SEQ ID No. 18. The protein of present invention provides Cucurbitaceae plants that provides fruits with an improved shelf life, or preferably fruits which stay green during storage for a time period of at least 4 or 5 weeks. Furthermore, the protein provides a plant the ability to maintain a green phenotype under stress conditions for a longer period in time, in comparison to plants that do not comprise the mutated stay green gene and protein. Preferably, said mutated stay green protein has more than 90% identity, preferably more than 94% identity, more preferably more than 96% identity, even more preferably more than 98% identity with SEQ ID No. 4 and SEQ ID No. 18.

According to a further aspect, the present invention relates to a nucleic acid sequence for providing Cucurbitaceae plants which provides fruits with an improved shelf life, wherein the nucleic acid sequence comprises SEQ ID No. 3 or SEQ ID No. 17, or having at least 87% sequence identity with SEQ ID No. 3 and SEQ ID No. 17. The nucleic acid sequence of present invention provides Cucurbitaceae plants which provides fruits with an improved shelf life, or preferably fruits which stay green during storage for a time period of at least 4 or 5 weeks. Preferably, said nucleic acid has more than 90% identity, preferably more than 94% identity, more preferably more than 96% identity, even more preferably more than 98% identity with SEQ ID NO. 3 and SEQ ID No. 17.

According to a further aspect, the present invention relates to use of protein or nucleic acid sequence as indicated above for providing Cucurbitaceae plants which provides fruits with an improved shelf life.

The invention is further elucidated in the illustrative examples below. In the examples, reference is made to figures wherein:

FIG. 1: A) shows a wild type *C. pepo* fruit (summer squash, zucchini) and *C. pepo* fruit according to the present invention comprising mutated stay green gene, approximately five weeks after harvest. The wild type *C. pepo* fruits (upper fruits) become yellow and the peel becomes more wrinkled. The *C. pepo* of present inventions (lower fruits) remains green and does not show any wrinkling of the skin.

B) shows wild type *C. pepo* fruit (winter squash, acorn type) and *C. pepo* fruit according to the present invention, approximately five weeks after harvest. The wild type *C. pepo* fruits (fruits on the left) become yellow in contrast to the *C. pepo* of present inventions (fruits on the right) that remain green.

Figure 2:
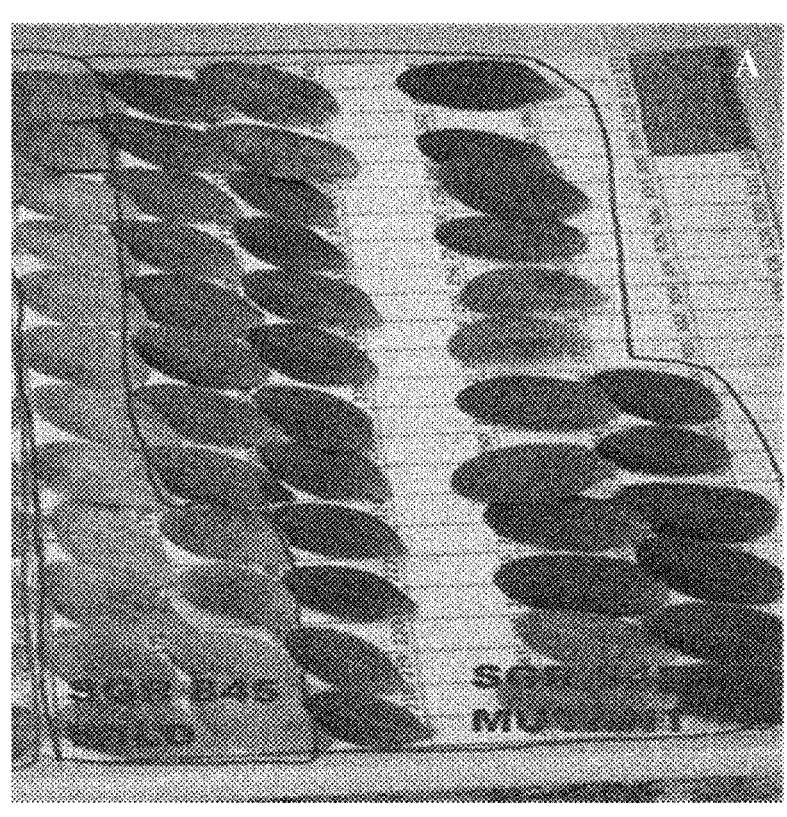
Figure 2:
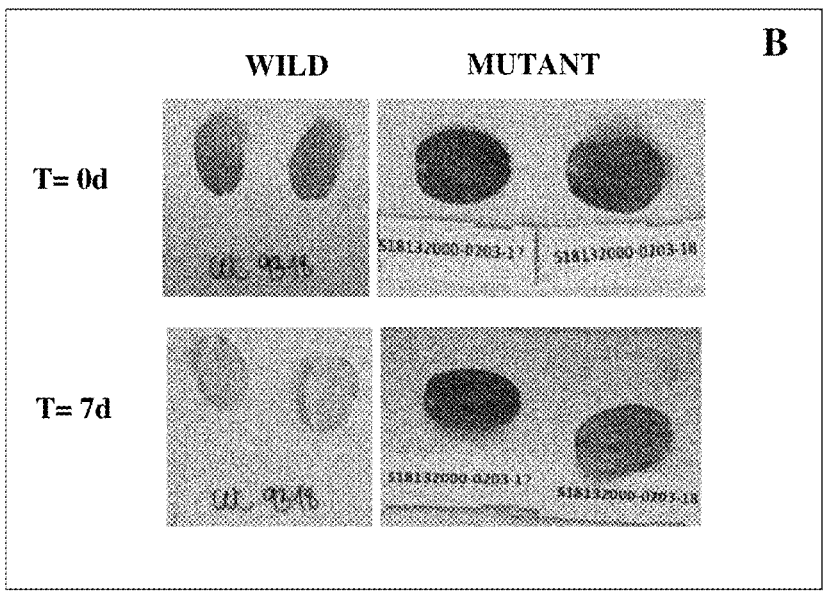

FIG. 2: A) shows leaves of a wild type *C. pepo* plant (WILD) and a *C. pepo* plant according to present invention comprising the mutated stay green gene (MUTANT). The leaves of a *C. pepo* plant of present invention remain green, whereas the wild type plant yellowing of the leaves is observed, after 2 weeks of storage after sampling.

B) shows leaves of a wild type *C. melo* (WILD) and a *C. melo* plant according to present invention comprising the mutated stay green gene (MUTANT). The leaves of a *C. melo* plant of present invention remain green, whereas the wild type plant yellowing of the leaves is observed, after a week (t=7 d) of storage after sampling.

Figure 3:

FIG. 3: shows a wild type *C. pepo* plant (right) and a *C. pepo* plant according to present invention (left). The plant and leaves of a Cucurbitaceae plant of present invention remain green, whereas at the wild type plant yellowing of the leaves and plant are observed.

FIG. 4: shows a sequence alignment of the stay green (SGR) protein in various Cucurbitaceae plants; *Cucurbita pepo, Cucurbita moschata, Cucurbita maxima, Cucurbita argyrosperma, Lagenaria siceraria, Citrullus lanatus*, and *Cucumis melo*. The alignment also includes the mutated SGR protein in a *Cucurbita pepo* or *Cucumis melo* ("Mutant") according to present invention. The alignments shows that the stay green protein is highly conserved within the Cucurbitaceae family.

EXAMPLE 1

About two thousand seeds of the *C. pepo* (breeding line SL0166) were treated with 0.75% (W/V) Ethyl Methane Sulfonate (EMS) for 16 hours. After rinsing the seeds several times with water, seeds were sown in peet blocks. After appearance of the primary leaf, the apical meristem was removed to induce the development of the lateral meristem. This procedure was repeated to induce outgrowth of the lateral meristem of the first side shoot. Samples were taken from the top of this developing shoot for further molecular analysis i.e. the detection of mutations in candidate genes as described by Van Eijk and Van Tunen in EP 1929039. The above EMS procedure was also done for *C. melo* to produce an EMS mutant population.

Plants derived from the EMS treatment comprising SEQ ID NO. 3 were grown in a greenhouse and fruits where harvested. The shelf life of the fruits was measured during approximately 5 weeks using the following scale: (1) Good colour (green); (2) Acceptable colour (somewhat lighter green); (3) Unacceptable colour (first occurrence of yellowing); (4) Unacceptable colour (yellowing); (5) Unacceptable colour (extreme yellowing). A conventional *C. pepo* fruit derived from a plant not comprising SEQ ID NO. 3 was also measured for approximately 5 weeks.

From the generated EMS population in *C. pepo* and *C. melo*, two mutants were selected; the *C. pepo* (S52F) and *C. melo* (R74K) mutants outperform the other SGR mutants in terms of maintaining a green colour over a longer period of time, thereby increasing the shelf life of the fruit. Furthermore, several other SGR mutants of *C. pepo* and *C. melo* were obtained and analysed for their stay green properties. Next to the S52F and R74K mutant, several other SGR mutants were analysed M1I, A13V, P25S, S30F, G45R, P170L, P188S, P205L, E221K and E251K. A1 these other mutants showed yellowing after 2 weeks in storage, comparable to the wild type, non mutated plants.

The *C. pepo* according to the invention stayed green during the time period of 4 weeks, with a continuous score (1). The conventional *C. pepo* shows a normal yellowish colour due to chlorophyll degradation during the 5 week test period, reaching score 4 after 5 weeks. FIG. 1A shows a picture with on the top the 5 weeks old conventional zucchini (*C. pepo*) fruit having a yellowish/orange colour, and below 5 weeks old zucchini according to the present invention having a full green colour. FIG. 1B shows a picture of squash fruit (*C. pepo*) after 5 weeks of storage, wherein the wild type fruits (fruits on the left) become yellow and the fruits according to present inventions (fruits on the right) remain green.

EXAMPLE 2

Seeds of plants of example 1 with a mutated stay green gene of SEQ ID No. 3 in homozygous form and wild type plants were grown till the cotyledon stage. The cotyledons were removed from the plantlets and placed in a plastic container covered with a glass plate. It can be considered that there was no air exchange possible between the content of the container and the environment. Cotyledons from *C. pepo* and *C. melo* plants of seeds that were harvested from the plant with and without the stay green comprising the S52F or R74K mutation, respectively, of present invention in the homozygous form were placed on the grid. After 2 weeks of storage, the picture as shown in FIG. 2 was visible for *C. pepo* (FIG. 2A) and *C. melo* (FIG. 2B); the leaves of a *C. pepo* plant of present invention remain green, whereas the wild type plant yellowing of the leaves is observed.

EXAMPLE 3

Leaves of a Cucurbitaceae plant, for example *C. pepo* and *C. melo*, which are in the lower part of the plant, become old and yellow, start to disintegrate when they are being covered by upper leaves. The disintegration of the leaf is, amongst others, caused by the inactivity and degradation of the chlorophyll. The chlorophyll is giving the green color to the leaf. Plants of the wild type (lacking the present mutant stay green gene), plants with the present stay green gene in heterozygous form, and plants with the present stay green gene comprising the mutation in homozygous form have been planted in the greenhouse. At mature stage of the plants (i.e. after 10 weeks) were placed next to each other. The result is shown in FIG. 3 for *C. pepo*. It is clear the plant with the present stay green gene in homozygous form is able to maintain its chlorophyll for a longer period. Likewise, it is expected that the plant containing this gene in homozygous form is able to be photosynthetic active for a longer period.

EXAMPLE 4

The sequence homology among stay green proteins of various Cucurbitaceae plants was analyzed using multiple alignment software. Stay green proteins of *Cucurbita pepo, Cucurbita moschata, Cucurbita maxima, Cucurbita argyrosperma, Lagenaria siceraria, Citrullus lanatus*, and *Cucumis melo* were analysed and it was shown that all stay green proteins share a high sequence homology of at least 87%, and in many cases more than 90% sequence identity between Cucurbitaceae plants (Table 1), see also FIG. 4.

TABLE 1

Shows the % sequence homology among stay green (SGR) proteins in Cucurbitaceae plants

| SGR Protein | C. pepo | C. moschata | C. maxima | C. argyro. | L. siceraria | C. lanatus | C. melo |
|---|---|---|---|---|---|---|---|
| C. pepo | — | 99.6 | 98.4 | 99.6 | 89.5 | 88.8 | 87.9 |
| C. moschata | 99.6 | — | 98.8 | 100.0 | 89.9 | 89.1 | 88.3 |
| C. maxima | 98.4 | 98.8 | — | 98.8 | 88.8 | 88.8 | 87.9 |
| C. argyro. | 99.6 | 100.0 | 98.8 | — | 89.9 | 89.1 | 88.3 |
| L. siceraria | 89.5 | 89.9 | 88.8 | 89.9 | — | 95.7 | 87.8 |

TABLE 1-continued

Shows the % sequence homology among stay green (SGR) proteins in Cucurbitaceae plants

| SGR Protein | C. pepo | C. moschata | C. maxima | C. argyro. | L. siceraria | C. lanatus | C. melo |
|---|---|---|---|---|---|---|---|
| C. lanatus | 88.8 | 89.1 | 88.8 | 89.1 | 95.7 | — | 87.8 |
| C. melo | 87.9 | 88.3 | 87.9 | 88.3 | 87.8 | 87.8 | — |

The invention claimed is:

1. A Cucurbitaceae plant comprising a mutated stay green gene in homozygous form, wherein said stay green gene encodes for a protein having at least 87% sequence identity with SEQ ID NO: 2 or SEQ ID NO: 6, and wherein the mutated stay green gene comprises at least one mutation in the stay green gene resulting in an amino acid substitution of Serine(S) to Phenylalanine (F) or Leucine (L) at amino acid position 52 or position 54 (S52F, S52L, S54F or S54L), and/or an amino acid substitution of Arginine (R) to Lysine (K) at amino acid position 72 or 74 (R72K or R74K) in the protein sequence of SEQ ID NO: 2 or SEQ ID NO: 6, respectively, and wherein said plant produces fruit with an increased shelf life compared to a wild type control plant.

2. The Cucurbitaceae plant according to claim 1, wherein said plant is selected from the group consisting of *Cucurbita pepo, Cucurbita moschata, Cucurbita maxima, Cucurbita argyrosperma, Lagenaria siceraria, Citrullus lanatus*, and *Cucumis melo*.

3. The Cucurbitaceae plant according to claim 1, wherein said plant is:

*Cucurbita pepo* wherein said mutated stay green gene encodes for a protein sequence of SEQ ID NO: 2 that comprises an amino acid substitution of Serine to Phenylalanine (S52F) at position 52, and/or an amino acid substitution of Arginine (R) to Lysine (K) at position 72 (R72K),

*Cucumis melo* wherein said mutated stay green gene encodes for a protein sequence of SEQ ID NO: 6 that comprises an amino acid substitution of Serine to Leucine (S54L) at position 54, and/or an amino acid substitution of Arginine (R) to Lysine (K) at position 74 (R74K),

*Cucurbita moschata* wherein said mutated stay green gene encodes for a protein sequence of SEQ ID NO: 12 that comprises an amino acid substitution of Serine to Phenylalanine (S52F) at position 52, and/or an amino acid substitution of Arginine (R) to Lysine (K) at position 72 (R72K),

*Cucurbita maxima* wherein said mutated stay green gene encodes for a protein sequence of SEQ ID NO: 10 that comprises an amino acid substitution of Serine to Phenylalanine (S52F) at position 52, and/or an amino acid substitution of Arginine (R) to Lysine (K) at position 72 (R72K),

*Cucurbita argyrosperma* wherein said mutated stay green gene encodes for a protein sequence of SEQ ID NO: 8 that comprises an amino acid substitution of Serine to Phenylalanine (S52F) at position 52, and/or an amino acid substitution of Arginine (R) to Lysine (K) at position 72 (R72K),

*Lagenaria siceraria* wherein said mutated stay green gene encodes for a protein sequence of SEQ ID NO: 14 that comprises an amino acid substitution of Serine to Leucine (S52L) at position 52, and/or an amino acid substitution of Arginine (R) to Lysine (K) at position 72 (R72K), or

*Citrullus lanatus* wherein said mutated stay green gene encodes for a protein sequence of SEQ ID NO: 16 that comprises an amino acid substitution of Serine to Leucine (S52L) at position 52, and/or an amino acid substitution of Arginine (R) to Lysine (K) at position 72 (R72K).

4. The Cucurbitaceae plant according to claim 1, wherein said plant is a *C. pepo* or *C. melo* and the mutated stay green gene encodes a protein comprising the amino acid sequence of SEQ ID NO: 4 or SEQ ID NO: 18, respectively.

5. The Cucurbitaceae plant according to claim 1, wherein said stay green gene is present in homozygous form.

6. The Cucurbitaceae plant according to claim 1, wherein said mutated stay green gene is obtainable from the deposit made in the National Collection of Industrial, Food and Marine Bacteria (NCIMB) under deposit number NCIMB 43480 or NCIMB 43513.

7. A seed, plant tissue, fruit, or plant part of the Cucurbitaceae plant according to claim 1, wherein the seed, plant tissue, fruit, or plant part comprises a mutated stay green gene, wherein said stay green gene encodes for a protein having at least 87% sequence identity with SEQ ID NO: 2 or SEQ ID NO: 6, and wherein the mutated stay green gene comprises at least one mutation in the stay green gene resulting in an amino acid substitution of Serine(S) to Phenylalanine (F) or Leucine (L) at amino acid position 52 or position 54 (S52F, S52L, S54F or S54L), and/or an amino acid substitution of Arginine (R) to Lysine (K) at amino acid position 72 or position 74 (R72K or R74K) in the protein sequence of SEQ ID NO: 2 or SEQ ID NO: 6, respectively.

8. The Cucurbitaceae plant according to claim 1, wherein said plant is *Cucurbita pepo* or *Cucumis melo*.

* * * * *

SEQUENCE LISTING

<160> NUMBER OF SEQ ID NOS: 18

<210> SEQ ID NO 1
<211> LENGTH: 762
<212> TYPE: DNA
<213> ORGANISM: Cucurbita pepo
<220> FEATURE:
<223> OTHER INFORMATION: >Cucurbita_pepo_SGR_CDS

<400> SEQUENCE: 1

```
atgagggggtt tgacggcgaa ttcttctgtt cttcttgctc cttcaaaccc atatcagaat      60
tcctctctgt ttccttctaa acgcaagtcc aagaagaaga accatgccat ggttcctgta     120
gcgaggctgt ttgggccggc catatttgaa gcttccaagt tgaaggttct gttttttagga     180 gtggatgaga agaagcatcc tggaaaattt cccaggactt acacgcttac acatagcgat     240
attacctcta aacttactct cgctatttct cagaccatta caactctca gctgcaagga     300 tggtataatt ggctacagag agatgaagtg gtgggagagt ggaagaaggt gaagggaaag     360
atgtcgcttc atgttcattg ccatatcagc ggcggccatt ttcttttaga tctctgtgct     420
aatctcagat acttcatctt ccgcaaagaa ctccctgtgg ttctgaatgc atttgtccat     480
ggagatgtgg acttgttcaa caattaccca gaattacagg acgcgttggt ctgggtttat     540
ttccattcga agatcccaga attcaacaaa gttgaatgct ggggcccact caagaatcca     600
gccccacctt cagctggact ggatgggtcc aattcagatg agcccatatg ggatatgggc     660
caaatggagc ggcccaaacc ttgccaagaa gactgctctt gttgcttccc aaccatccct     720
tccatttcat ggtcacccaa aaatgagttg gagagtacct ga                       762
```

<210> SEQ ID NO 2
<211> LENGTH: 253
<212> TYPE: PRT
<213> ORGANISM: Cucurbita pepo
<220> FEATURE:
<223> OTHER INFORMATION: >Cucurbita_pepo_SGR_Protein

<400> SEQUENCE: 2

```
Met Arg Gly Leu Thr Ala Asn Ser Ser Val Leu Leu Ala Pro Ser Asn
1               5                   10                  15

Pro Tyr Gln Asn Ser Ser Leu Phe Pro Ser Lys Arg Lys Ser Lys Lys
                20                  25                  30

Lys Asn His Ala Met Val Pro Val Ala Arg Leu Phe Gly Pro Ala Ile
            35                  40                  45

Phe Glu Ala Ser Lys Leu Lys Val Leu Phe Leu Gly Val Asp Glu Lys
        50                  55                  60

Lys His Pro Gly Lys Phe Pro Arg Thr Tyr Thr Leu Thr His Ser Asp
65                  70                  75                  80

Ile Thr Ser Lys Leu Thr Leu Ala Ile Ser Gln Thr Ile Asn Asn Ser
                85                  90                  95

Gln Leu Gln Gly Trp Tyr Asn Trp Leu Gln Arg Asp Glu Val Val Gly
```

-continued

```
                    100               105               110
Glu Trp Lys Lys Val Lys Gly Lys Met Ser Leu His Val His Cys His
        115               120               125

Ile Ser Gly Gly His Phe Leu Leu Asp Leu Cys Ala Asn Leu Arg Tyr
    130               135               140

Phe Ile Phe Arg Lys Glu Leu Pro Val Val Leu Asn Ala Phe Val His
145               150               155               160

Gly Asp Val Asp Leu Phe Asn Asn Tyr Pro Glu Leu Gln Asp Ala Leu
                165               170               175

Val Trp Val Tyr Phe His Ser Lys Ile Pro Glu Phe Asn Lys Val Glu
                180               185               190

Cys Trp Gly Pro Leu Lys Asn Pro Ala Pro Ser Ala Gly Leu Asp
            195               200               205

Gly Ser Asn Ser Asp Glu Pro Ile Trp Asp Met Gly Gln Met Glu Arg
    210               215               220

Pro Lys Pro Cys Gln Glu Asp Cys Ser Cys Cys Phe Pro Thr Ile Pro
225               230               235               240

Ser Ile Ser Trp Ser Pro Lys Asn Glu Leu Glu Ser Thr
                245               250
```

```
<210> SEQ ID NO 3
<211> LENGTH: 762
<212> TYPE: DNA
<213> ORGANISM: Cucurbita pepo
<220> FEATURE:
<223> OTHER INFORMATION: >Cucurbita_pepo_Mutant_SGR_CDS

<400> SEQUENCE: 3
atgaggggtt tgacggcgaa ttcttctgtt cttcttgctc cttcaaaccc atatcagaat     60
tcctctctgt ttccttctaa acgcaagtcc aagaagaaga accatgccat ggttcctgta    120
gcgaggctgt ttgggccggc catatttgaa gctttcaagt tgaaggttct gttttttagga   180 gtggatgaga agaagcatcc tggaaaattt cccaggactt acacgcttac acatagcgat    240
attacctcta aacttactct cgctatttct cagaccatta caactctca gctgcaagga     300 tggtataatt ggctacagag agatgaagtg gtgggagagt ggaagaaggt gaagggaaag    360
atgtcgcttc atgttcattg ccatatcagc ggcggccatt ttcttttaga tctctgtgct    420
aatctcagat acttcatctt ccgcaaagaa ctccctgtgg ttctgaatgc atttgtccat    480
ggagatgtgg acttgttcaa caattacccca gaattacagg acgcgttggt ctgggtttat    540
ttccattcga agatcccaga attcaacaaa gttgaatgct ggggcccact caagaatcca    600
gccccacctt cagctggact ggatgggtcc aattcagatg agcccatatg ggatatgggc    660
caaatggagc ggcccaaacc ttgccaagaa gactgctctt gttgcttccc aaccatccct    720
tccatttcat ggtcacccaa aaatgagttg gagagtacct ga                      762
```

```
<210> SEQ ID NO 4
<211> LENGTH: 253
<212> TYPE: PRT
<213> ORGANISM: Cucurbita pepo
<220> FEATURE:
<223> OTHER INFORMATION: >Cucurbita_pepo_Mutant_SGR_Protein

<400> SEQUENCE: 4

Met Arg Gly Leu Thr Ala Asn Ser Ser Val Leu Leu Ala Pro Ser Asn
1               5               10               15

Pro Tyr Gln Asn Ser Ser Leu Phe Pro Ser Lys Arg Lys Ser Lys Lys
```

```
                   20              25              30

Lys Asn His Ala Met Val Pro Val Ala Arg Leu Phe Gly Pro Ala Ile
        35              40              45

Phe Glu Ala Phe Lys Leu Lys Val Leu Phe Leu Gly Val Asp Glu Lys
    50              55              60

Lys His Pro Gly Lys Phe Pro Arg Thr Tyr Thr Leu Thr His Ser Asp
65              70              75              80

Ile Thr Ser Lys Leu Thr Leu Ala Ile Ser Gln Thr Ile Asn Asn Ser
            85              90              95

Gln Leu Gln Gly Trp Tyr Asn Trp Leu Gln Arg Asp Glu Val Val Gly
            100             105             110

Glu Trp Lys Lys Val Lys Gly Lys Met Ser Leu His Val His Cys His
        115             120             125

Ile Ser Gly Gly His Phe Leu Leu Asp Leu Cys Ala Asn Leu Arg Tyr
        130             135             140

Phe Ile Phe Arg Lys Glu Leu Pro Val Val Leu Asn Ala Phe Val His
145             150             155             160

Gly Asp Val Asp Leu Phe Asn Asn Tyr Pro Glu Leu Gln Asp Ala Leu
            165             170             175

Val Trp Val Tyr Phe His Ser Lys Ile Pro Glu Phe Asn Lys Val Glu
            180             185             190

Cys Trp Gly Pro Leu Lys Asn Pro Ala Pro Pro Ser Ala Gly Leu Asp
            195             200             205

Gly Ser Asn Ser Asp Glu Pro Ile Trp Asp Met Gly Gln Met Glu Arg
        210             215             220

Pro Lys Pro Cys Gln Glu Asp Cys Ser Cys Cys Phe Pro Thr Ile Pro
225             230             235             240

Ser Ile Ser Trp Ser Pro Lys Asn Glu Leu Glu Ser Thr
            245             250
```

```
<210> SEQ ID NO 5
<211> LENGTH: 774
<212> TYPE: DNA
<213> ORGANISM: Cucumis melo
<220> FEATURE:
<223> OTHER INFORMATION: >Cucumis_melo_SGR_CDS

<400> SEQUENCE: 5
atgagggttt tgactagtaa ttcttctcct cttcttgttc cttcttcaaa cccttatcag      60
gattcttctt ctctcttcct ctgtaaacgc aaatccaagg agaaaaacca cagaatggtt     120
cctatggcga gattgtttgg gccagccata tttgaagctt cgaagctaaa ggttctgttt     180
ttaggggtgg atgagaagaa acatccaggc aaatttccaa ggacttatac gcttacacat     240
agtgatatta cttctaaact tactcttgcc atttctcaat ccattaacaa ttctcagtta     300
caaggatggt ataattggct tcaaagggat gaagtggtag cagaatggaa gaaagtacag     360
gggaaaatgt cccttcatgt tcattgtcat atcagtggtg gccatttct tctagatctc      420 tgtgctaatc tccgatactt catctttcgc agagaacttc ctgtggtgct gaatgctttc     480
gtccatggag atgtggactt gttcaagaat tacccagagc tacaagaggc tatggtttgg     540
gtttatttcc actccaaaat tccggaattc aacaaagtag aatgctgggg cccactaaag     600
gatccagccc caccttcaag tgggcttgat gggcggccca atcagatga gcccatgtgg      660 gaattgagcc ggatggagcg gcccaaacct tgccaagaag actgcaattg ttgcttccca     720 accatcccctt ccatttcatg gtcccccaag aacagtgagt tggagagcac gtga          774
```

```
<210> SEQ ID NO 6
<211> LENGTH: 257
<212> TYPE: PRT
<213> ORGANISM: Cucumis melo
<220> FEATURE:
<223> OTHER INFORMATION: >Cucumis_melo_SGR_Protein

<400> SEQUENCE: 6

Met Arg Val Leu Thr Ser Asn Ser Ser Pro Leu Leu Val Pro Ser Ser
1               5                   10                  15

Asn Pro Tyr Gln Asp Ser Ser Ser Leu Phe Leu Cys Lys Arg Lys Ser
            20                  25                  30

Lys Glu Lys Asn His Arg Met Val Pro Met Ala Arg Leu Phe Gly Pro
        35                  40                  45

Ala Ile Phe Glu Ala Ser Lys Leu Lys Val Leu Phe Leu Gly Val Asp
    50                  55                  60

Glu Lys Lys His Pro Gly Lys Phe Pro Arg Thr Tyr Thr Leu Thr His
65                  70                  75                  80

Ser Asp Ile Thr Ser Lys Leu Thr Leu Ala Ile Ser Gln Ser Ile Asn
                85                  90                  95

Asn Ser Gln Leu Gln Gly Trp Tyr Asn Trp Leu Gln Arg Asp Glu Val
            100                 105                 110

Val Ala Glu Trp Lys Lys Val Gln Gly Lys Met Ser Leu His Val His
            115                 120                 125

Cys His Ile Ser Gly Gly His Phe Leu Leu Asp Leu Cys Ala Asn Leu
    130                 135                 140

Arg Tyr Phe Ile Phe Arg Arg Glu Leu Pro Val Val Leu Asn Ala Phe
145                 150                 155                 160

Val His Gly Asp Val Asp Leu Phe Lys Asn Tyr Pro Glu Leu Gln Glu
                165                 170                 175

Ala Met Val Trp Val Tyr Phe His Ser Lys Ile Pro Glu Phe Asn Lys
            180                 185                 190

Val Glu Cys Trp Gly Pro Leu Lys Asp Pro Ala Pro Pro Ser Ser Gly
            195                 200                 205

Leu Asp Gly Arg Pro Lys Ser Asp Glu Pro Met Trp Glu Leu Ser Arg
    210                 215                 220

Met Glu Arg Pro Lys Pro Cys Gln Glu Asp Cys Asn Cys Cys Phe Pro
225                 230                 235                 240

Thr Ile Pro Ser Ile Ser Trp Ser Pro Lys Asn Ser Glu Leu Glu Ser
                245                 250                 255

Thr

<210> SEQ ID NO 7
<211> LENGTH: 762
<212> TYPE: DNA
<213> ORGANISM: Cucurbita argyrosperma
<220> FEATURE:
<223> OTHER INFORMATION: >Cucurbita_argyrosperma_SGR_CDS

<400> SEQUENCE: 7
atgaggggtt tgacggcgaa ttcttctgtt cttcttgctc cttcaaaccc atatcagaat        60
tcctctctgt ttccttctaa acgcaagtcc aagaagaaga accatgccat ggttcctgta       120
gcgaggctgt ttgggccggc catatttgaa gcttccaagt taaaggttct gtttttagga       180
gtggatgaaa agaagcatcc tggcaaattt cccaggactt acacgcttac acatagcgat       240
```

```
attacctcta aacttactct cgctatttct cagaccatta acaactctca gctgcaagga      300
tggtataatt ggctacaaag agatgaagtg gtgggagagt ggaagaaggt gaagggaaag      360
atgtcgcttc atgttcattg ccatatcagc ggcggccatt ttcttttaga tctctgtgct      420
aatctcagat acttcatctt ccgcaaagaa ctccctgtgg ttctgaatgc gtttgtccat      480
ggagatgtgg acttgttcaa caattaccca gaattacagg acgcgttggt ctgggtttat      540
ttccattcga agatcccaga attcaacaaa gttgaatgct ggggcccact caaggatcca      600
gccccacctt cagctggact tgatgggtcc aattcagatg agcccatatg ggatatgggc      660
caaatggagc ggcccaaacc ttgccaagaa gactgctctt gttgcttccc aaccatccct      720
tccatttcat ggtcacccaa aaatgagttg gagagtacct ga                       762
```

<210> SEQ ID NO 8
<211> LENGTH: 253
<212> TYPE: PRT
<213> ORGANISM: Cucurbita argyrosperma
<220> FEATURE:
<223> OTHER INFORMATION: >Cucurbita_argyrosperma_SGR_Protein

<400> SEQUENCE: 8

```
Met Arg Gly Leu Thr Ala Asn Ser Ser Val Leu Leu Ala Pro Ser Asn
1               5                   10                  15

Pro Tyr Gln Asn Ser Ser Leu Phe Pro Ser Lys Arg Lys Ser Lys Lys
                20                  25                  30

Lys Asn His Ala Met Val Pro Val Ala Arg Leu Phe Gly Pro Ala Ile
            35                  40                  45

Phe Glu Ala Ser Lys Leu Lys Val Leu Phe Leu Gly Val Asp Glu Lys
        50                  55                  60

Lys His Pro Gly Lys Phe Pro Arg Thr Tyr Thr Leu Thr His Ser Asp
65                  70                  75                  80

Ile Thr Ser Lys Leu Thr Leu Ala Ile Ser Gln Thr Ile Asn Asn Ser
                85                  90                  95

Gln Leu Gln Gly Trp Tyr Asn Trp Leu Gln Arg Asp Glu Val Val Gly
            100                 105                 110

Glu Trp Lys Lys Val Lys Gly Lys Met Ser Leu His Val His Cys His
            115                 120                 125

Ile Ser Gly Gly His Phe Leu Leu Asp Leu Cys Ala Asn Leu Arg Tyr
        130                 135                 140

Phe Ile Phe Arg Lys Glu Leu Pro Val Val Leu Asn Ala Phe Val His
145                 150                 155                 160

Gly Asp Val Asp Leu Phe Asn Asn Tyr Pro Glu Leu Gln Asp Ala Leu
                165                 170                 175

Val Trp Val Tyr Phe His Ser Lys Ile Pro Glu Phe Asn Lys Val Glu
            180                 185                 190

Cys Trp Gly Pro Leu Lys Asp Pro Ala Pro Ser Ala Gly Leu Asp
            195                 200                 205

Gly Ser Asn Ser Asp Glu Pro Ile Trp Asp Met Gly Gln Met Glu Arg
        210                 215                 220

Pro Lys Pro Cys Gln Glu Asp Cys Ser Cys Cys Phe Pro Thr Ile Pro
225                 230                 235                 240

Ser Ile Ser Trp Ser Pro Lys Asn Glu Leu Glu Ser Thr
                245                 250
```

<210> SEQ ID NO 9
<211> LENGTH: 762

-continued

```
<212> TYPE: DNA
<213> ORGANISM: Cucurbita maxima
<220> FEATURE:
<223> OTHER INFORMATION: >Cucurbita_maxima_SGR_CDS

<400> SEQUENCE: 9
atgaggggtt tgacggcgaa ttcttctgtt cttcttgctc cttcaaaccc atatcagagt      60
tcctctctgt ttccttctaa acgcaagtcc aagaagaaga accatgctat ggttcctgta     120
gcgaggctgt ttgggccggc catatttgaa gcttccaagt tgaaggttct gtttttagga     180
gtggatgaga agaagcatcc tggaaaattt cccaggactt acacgcttac acacagcgat     240
attacctcta aacttactct cgctatttct cagaccatta caactctca gctgcaagga      300 tggtataatt ggctacaaag agatgaagtg gtgggagagt ggaagaaggt gaagggaaag     360
atgtcgcttc atgttcattg ccatatcagc ggcggccatt ttcttttaga tctctgtgct     420
aatctcagat acttcatctt ccgcaaagaa ctccctgtgg ttctgaatgc gtttgtccat     480
ggagatgtgg attttattcaa caattaccca gaattacagg atgcgttggt ctgggtttat     540
ttccattcaa agatcccaga attcaacaaa gttgaatgct ggggcccact caaggatcca     600
gccccacctt cagctggact tgatgggtcc aattcagacg ggtccatatg ggatatgggc     660
caaatggagc ggcccaaacc ttgccaagaa gactgctctt gttgcttccc aaccatccct     720
tccatttcat ggtcacccaa aaatgagttg gagagtacct ga                        762
```

```
<210> SEQ ID NO 10
<211> LENGTH: 253
<212> TYPE: PRT
<213> ORGANISM: Cucurbita maxima
<220> FEATURE:
<223> OTHER INFORMATION: >Cucurbita_maxima_SGR_Protein

<400> SEQUENCE: 10

Met Arg Gly Leu Thr Ala Asn Ser Ser Val Leu Leu Ala Pro Ser Asn
1               5                   10                  15

Pro Tyr Gln Ser Ser Ser Leu Phe Pro Ser Lys Arg Lys Ser Lys Lys
                20                  25                  30

Lys Asn His Ala Met Val Pro Val Ala Arg Leu Phe Gly Pro Ala Ile
            35                  40                  45

Phe Glu Ala Ser Lys Leu Lys Val Leu Phe Leu Gly Val Asp Glu Lys
        50                  55                  60

Lys His Pro Gly Lys Phe Pro Arg Thr Tyr Thr Leu Thr His Ser Asp
65                  70                  75                  80

Ile Thr Ser Lys Leu Thr Leu Ala Ile Ser Gln Thr Ile Asn Asn Ser
                85                  90                  95

Gln Leu Gln Gly Trp Tyr Asn Trp Leu Gln Arg Asp Glu Val Val Gly
                100                 105                 110

Glu Trp Lys Lys Val Lys Gly Lys Met Ser Leu His Val His Cys His
            115                 120                 125

Ile Ser Gly Gly His Phe Leu Leu Asp Leu Cys Ala Asn Leu Arg Tyr
            130                 135                 140

Phe Ile Phe Arg Lys Glu Leu Pro Val Val Leu Asn Ala Phe Val His
145                 150                 155                 160

Gly Asp Val Asp Leu Phe Asn Asn Tyr Pro Glu Leu Gln Asp Ala Leu
                165                 170                 175

Val Trp Val Tyr Phe His Ser Lys Ile Pro Glu Phe Asn Lys Val Glu
                180                 185                 190
```

```
Cys Trp Gly Pro Leu Lys Asp Pro Ala Pro Pro Ser Ala Gly Leu Asp
        195             200             205

Gly Ser Asn Ser Asp Gly Ser Ile Trp Asp Met Gly Gln Met Glu Arg
    210             215             220

Pro Lys Pro Cys Gln Glu Asp Cys Ser Cys Cys Phe Pro Thr Ile Pro
225             230             235             240

Ser Ile Ser Trp Ser Pro Lys Asn Glu Leu Glu Ser Thr
            245             250
```

```
<210> SEQ ID NO 11
<211> LENGTH: 762
<212> TYPE: DNA
<213> ORGANISM: Cucurbita moschata
<220> FEATURE:
<223> OTHER INFORMATION: >Cucurbita_moschata_SGR_CDS

<400> SEQUENCE: 11
atgaggggtt tgacggcgaa ttcttctgtt cttcttgctc cttcaaaccc atatcagaat      60
tcctctctgt ttccttctaa acgcaagtcc aagaagaaga accatgccat ggttcctgta     120
gcgaggctgt ttgggccggc catatttgaa gcttccaagt taaaggttct gtttttagga     180
gtggatgaaa agaagcatcc tggcaaattt cccaggactt acacgcttac acatagcgat     240
attacctcta aacttactct cgctatttct cagaccatta caactctca gctgcaagga     300 tggtataatt ggctacaaag agatgaagtg gtgggagagt ggaagaaggt gaagggaaag     360
atgtcgcttc atgttcattg ccatatcagc ggcggccatt ttcttttaga tctctgtgct     420
aatctcagat acttcatctt ccgcaaagaa ctccctgtgg ttctgaatgc gtttgtccat     480
ggagatgtgg acttgttcaa caattaccca gaattacagg acgcgttggt ctgggtttat     540
ttccattcga agatcccaga attcaacaaa gttgaatgct ggggcccact caaggatcca     600
gccccacctt cagctggact tgatgggtcc aattcagatg agcccatatg ggatatgggc     660
caaatggagc ggcccaaacc ttgccaagaa gactgctctt gttgcttccc aaccatccct     720
tccatttcat ggtcacccaa aaatgagttg gagagtacct ga                       762
```

```
<210> SEQ ID NO 12
<211> LENGTH: 253
<212> TYPE: PRT
<213> ORGANISM: Cucurbita moschata
<220> FEATURE:
<223> OTHER INFORMATION: >Cucurbita_moschata_SGR_Protein

<400> SEQUENCE: 12

Met Arg Gly Leu Thr Ala Asn Ser Ser Val Leu Leu Ala Pro Ser Asn
1               5               10              15

Pro Tyr Gln Asn Ser Ser Leu Phe Pro Ser Lys Arg Lys Ser Lys Lys
            20              25              30

Lys Asn His Ala Met Val Pro Val Ala Arg Leu Phe Gly Pro Ala Ile
        35              40              45

Phe Glu Ala Ser Lys Leu Lys Val Leu Phe Leu Gly Val Asp Glu Lys
    50              55              60

Lys His Pro Gly Lys Phe Pro Arg Thr Tyr Thr Leu Thr His Ser Asp
65              70              75              80

Ile Thr Ser Lys Leu Thr Leu Ala Ile Ser Gln Thr Ile Asn Asn Ser
            85              90              95

Gln Leu Gln Gly Trp Tyr Asn Trp Leu Gln Arg Asp Glu Val Val Gly
            100             105             110
```

-continued

```
Glu Trp Lys Lys Val Lys Gly Lys Met Ser Leu His Val His Cys His
        115             120             125

Ile Ser Gly Gly His Phe Leu Leu Asp Leu Cys Ala Asn Leu Arg Tyr
    130             135             140

Phe Ile Phe Arg Lys Glu Leu Pro Val Val Leu Asn Ala Phe Val His
145             150             155             160

Gly Asp Val Asp Leu Phe Asn Asn Tyr Pro Glu Leu Gln Asp Ala Leu
                165             170             175

Val Trp Val Tyr Phe His Ser Lys Ile Pro Glu Phe Asn Lys Val Glu
            180             185             190

Cys Trp Gly Pro Leu Lys Asp Pro Ala Pro Pro Ser Ala Gly Leu Asp
            195             200             205

Gly Ser Asn Ser Asp Glu Pro Ile Trp Asp Met Gly Gln Met Glu Arg
        210             215             220

Pro Lys Pro Cys Gln Glu Asp Cys Ser Cys Cys Phe Pro Thr Ile Pro
225             230             235             240

Ser Ile Ser Trp Ser Pro Lys Asn Glu Leu Glu Ser Thr
                245             250
```

```
<210> SEQ ID NO 13
<211> LENGTH: 768
<212> TYPE: DNA
<213> ORGANISM: Lagenaria siceraria
<220> FEATURE:
<223> OTHER INFORMATION: >Lagenaria_siceraria_SGR_CDS

<400> SEQUENCE: 13
atgagggttt tgacgactaa ttcttctgtt cttcttgttc cttcaaaccc atatcagaat        60
tcttctttct tcccctgtaa acgcaaatcc aagaagaaca accatgccat agtccctgtg       120
gcgagactat ttgggccagc tatatttgaa gcttcgaagc tgaaggttct gtttttagga       180
gtggatgaga agaagcatcc agggaaattt ccaaggactt atacgcttac acatagcgat       240
ataacttcta aactcactct tgccatttct cagtccatta caactctca gttacaagga       300 tggtataatt ggctgcaaag ggatgaagtg gtgggagaat ggaagaaagt gaagggaaaa       360
atgtctcttc atgttcattg ccatattagt ggtggccatt ttcttttaga tctttgtgct       420
aatctcagat acttcatctt tcgcaaagaa cttcctgtgg tgctgaatgc ttttgtgcat       480
ggagatgtgg acttgttcaa caattaccca gaattacagg aggctttggt ttgggtttat       540
ttccactcca aaattccgga attcaataaa gtagaatgtt ggggcccaat aaaggatcca       600 gccccaccttt caactgggcc caaatcagat gagggcactc aaagccagcc catgtgggat       660
ttgggccggc tggagcggcc caaaccttgc caagaagact gcaattgttg cttcccaacc       720
atcccttcca tttcatggtc ccccaaaaat gagttggaga gcacctga                    768
```

```
<210> SEQ ID NO 14
<211> LENGTH: 255
<212> TYPE: PRT
<213> ORGANISM: Lagenaria siceraria
<220> FEATURE:
<223> OTHER INFORMATION: >Lagenaria_siceraria_SGR_Protein

<400> SEQUENCE: 14

Met Arg Val Leu Thr Thr Asn Ser Ser Val Leu Leu Val Pro Ser Asn
1               5               10              15

Pro Tyr Gln Asn Ser Ser Phe Phe Pro Cys Lys Arg Lys Ser Lys Lys
                20              25              30
```

```
Asn Asn His Ala Ile Val Pro Val Ala Arg Leu Phe Gly Pro Ala Ile
        35              40              45

Phe Glu Ala Ser Lys Leu Lys Val Leu Phe Leu Gly Val Asp Glu Lys
    50              55              60

Lys His Pro Gly Lys Phe Pro Arg Thr Tyr Thr Leu Thr His Ser Asp
65              70              75              80

Ile Thr Ser Lys Leu Thr Leu Ala Ile Ser Gln Ser Ile Asn Asn Ser
            85              90              95

Gln Leu Gln Gly Trp Tyr Asn Trp Leu Gln Arg Asp Glu Val Val Gly
            100             105             110

Glu Trp Lys Lys Val Lys Gly Lys Met Ser Leu His Val His Cys His
        115             120             125

Ile Ser Gly Gly His Phe Leu Leu Asp Leu Cys Ala Asn Leu Arg Tyr
    130             135             140

Phe Ile Phe Arg Lys Glu Leu Pro Val Val Leu Asn Ala Phe Val His
145             150             155             160

Gly Asp Val Asp Leu Phe Asn Asn Tyr Pro Glu Leu Gln Glu Ala Leu
            165             170             175

Val Trp Val Tyr Phe His Ser Lys Ile Pro Glu Phe Asn Lys Val Glu
            180             185             190

Cys Trp Gly Pro Ile Lys Asp Pro Ala Pro Pro Ser Thr Gly Pro Lys
            195             200             205

Ser Asp Glu Gly Thr Gln Ser Gln Pro Met Trp Asp Leu Gly Arg Leu
    210             215             220

Glu Arg Pro Lys Pro Cys Gln Glu Asp Cys Asn Cys Cys Phe Pro Thr
225             230             235             240

Ile Pro Ser Ile Ser Trp Ser Pro Lys Asn Glu Leu Glu Ser Thr
            245             250             255
```

```
<210> SEQ ID NO 15
<211> LENGTH: 777
<212> TYPE: DNA
<213> ORGANISM: Citrullus lanatus
<220> FEATURE:
<223> OTHER INFORMATION: >Citrullus_lanatus_SGR_CDS

<400> SEQUENCE: 15
atgagggttt tgacgactaa ttcttctgtt cttcttgttc cttcaaaccc atatcagaat        60
tcttctctct tcccctgtaa acgcaaatcc aagaagaaca accatgccat agtccctatg       120
gccaggctat ttgggccagc tatatttgaa gcttcgaagc tgaaggttct gtttttagga       180
gtggatgaga agaagcatcc aggaaaattt ccaagaactt atacgctaac tcatagcgat       240
ataacttcta aactcactct tgccatttct cagtccatta caactctca gttacaagga        300 tggtacaatt ggctgcaaag ggatgaagtg gtaggagaat ggaagaaagt gaaaggaaaa       360
atgtctcttc atgttcattg ccatattagt ggtggccatt ttcttttaga tctttgtgct       420
aaactcagat acttcatctt tcgcaaagaa cttcctgtgg tgctgaatgc ttttgtccat       480
ggagatgtgg acttgttcaa caattaccca gaattacaag aggctttggt ttgggtttat       540
tttcactcca atattccaga attcaacaaa gtggaatgtt ggggcccatt aaaggatcca       600
gccccacctt caactgggcc ctatgggccc aagtcagatg agcccactca aagccagtcc       660
atgtgggatt tgggccggct ggagcggccc aaaccttgcc aagaagattg caattgttgc       720
ttcccaacca tcccttccat ttcatggtcc ccccaaaatg agttggagag cacctga         777
```

-continued

```
<210> SEQ ID NO 16
<211> LENGTH: 258
<212> TYPE: PRT
<213> ORGANISM: Citrullus lanatus
<220> FEATURE:
<223> OTHER INFORMATION: >Citrullus_lanatus_SGR_Protein

<400> SEQUENCE: 16

Met Arg Val Leu Thr Thr Asn Ser Ser Val Leu Leu Val Pro Ser Asn
1               5                   10                  15

Pro Tyr Gln Asn Ser Ser Leu Phe Pro Cys Lys Arg Lys Ser Lys Lys
                20                  25                  30

Asn Asn His Ala Ile Val Pro Met Ala Arg Leu Phe Gly Pro Ala Ile
            35                  40                  45

Phe Glu Ala Ser Lys Leu Lys Val Leu Phe Leu Gly Val Asp Glu Lys
        50                  55                  60

Lys His Pro Gly Lys Phe Pro Arg Thr Tyr Thr Leu Thr His Ser Asp
65                  70                  75                  80

Ile Thr Ser Lys Leu Thr Leu Ala Ile Ser Gln Ser Ile Asn Asn Ser
                85                  90                  95

Gln Leu Gln Gly Trp Tyr Asn Trp Leu Gln Arg Asp Glu Val Val Gly
            100                 105                 110

Glu Trp Lys Lys Val Lys Gly Lys Met Ser Leu His Val His Cys His
            115                 120                 125

Ile Ser Gly Gly His Phe Leu Leu Asp Leu Cys Ala Lys Leu Arg Tyr
        130                 135                 140

Phe Ile Phe Arg Lys Glu Leu Pro Val Val Leu Asn Ala Phe Val His
145                 150                 155                 160

Gly Asp Val Asp Leu Phe Asn Asn Tyr Pro Glu Leu Gln Glu Ala Leu
                165                 170                 175

Val Trp Val Tyr Phe His Ser Asn Ile Pro Glu Phe Asn Lys Val Glu
            180                 185                 190

Cys Trp Gly Pro Leu Lys Asp Pro Ala Pro Pro Ser Thr Gly Pro Tyr
            195                 200                 205

Gly Pro Lys Ser Asp Glu Pro Thr Gln Ser Gln Ser Met Trp Asp Leu
        210                 215                 220

Gly Arg Leu Glu Arg Pro Lys Pro Cys Gln Glu Asp Cys Asn Cys Cys
225                 230                 235                 240

Phe Pro Thr Ile Pro Ser Ile Ser Trp Ser Pro Gln Asn Glu Leu Glu
                245                 250                 255

Ser Thr

<210> SEQ ID NO 17
<211> LENGTH: 774
<212> TYPE: DNA
<213> ORGANISM: Cucumis melo
<220> FEATURE:
<223> OTHER INFORMATION: cDNA SGR mutant Cucumis Melo

<400> SEQUENCE: 17
atgagggttt tgactagtaa ttcttctcct cttcttgttc cttcttcaaa cccttatcag      60
gattcttctt ctctcttcct ctgtaaacgc aaatccaagg agaaaaacca cagaatggtt     120
cctatggcga gattgtttgg gccagccata tttgaagctt cgaagctaaa ggttctgttt     180
ttaggggtgg atgagaagaa acatccaggc aaatttccaa agacttatac gcttacacat     240
agtgatatta cttctaaact tactcttgcc atttctcaat ccattaacaa ttctcagtta     300
```

-continued

```
caaggatggt ataattggct tcaaagggat gaagtggtag cagaatggaa gaaagtacag      360
gggaaaatgt cccttcatgt tcattgtcat atcagtggtg gccattttct tctagatctc      420
tgtgctaatc tccgatactt catctttcgc agagaacttc ctgtggtgct gaatgctttc      480
gtccatggag atgtggactt gttcaagaat tacccagagc tacaagaggc tatggtttgg      540
gtttatttcc actccaaaat tccggaattc aacaaagtag aatgctgggg cccactaaag      600
gatccagccc caccttcaag tgggcttgat gggcggccca aatcagatga gcccatgtgg      660
gaattgagcc ggatggagcg gcccaaacct tgccaagaag actgcaattg ttgcttccca      720
accatccctt ccatttcatg gtcccccaag aacagtgagt tggagagcac gtga           774
```

<210> SEQ ID NO 18
<211> LENGTH: 257
<212> TYPE: PRT
<213> ORGANISM: Cucumis melo
<220> FEATURE:
<223> OTHER INFORMATION: protein SGR mutant Cucumis Melo

<400> SEQUENCE: 18

```
Met Arg Val Leu Thr Ser Asn Ser Ser Pro Leu Leu Val Pro Ser Ser
1               5                   10                  15

Asn Pro Tyr Gln Asp Ser Ser Ser Leu Phe Leu Cys Lys Arg Lys Ser
            20                  25                  30

Lys Glu Lys Asn His Arg Met Val Pro Met Ala Arg Leu Phe Gly Pro
        35                  40                  45

Ala Ile Phe Glu Ala Ser Lys Leu Lys Val Leu Phe Leu Gly Val Asp
    50                  55                  60

Glu Lys Lys His Pro Gly Lys Phe Pro Lys Thr Tyr Thr Leu Thr His
65                  70                  75                  80

Ser Asp Ile Thr Ser Lys Leu Thr Leu Ala Ile Ser Gln Ser Ile Asn
                85                  90                  95

Asn Ser Gln Leu Gln Gly Trp Tyr Asn Trp Leu Gln Arg Asp Glu Val
            100                 105                 110

Val Ala Glu Trp Lys Lys Val Gln Gly Lys Met Ser Leu His Val His
        115                 120                 125

Cys His Ile Ser Gly Gly His Phe Leu Leu Asp Leu Cys Ala Asn Leu
    130                 135                 140

Arg Tyr Phe Ile Phe Arg Arg Glu Leu Pro Val Val Leu Asn Ala Phe
145                 150                 155                 160

Val His Gly Asp Val Asp Leu Phe Lys Asn Tyr Pro Glu Leu Gln Glu
                165                 170                 175

Ala Met Val Trp Val Tyr Phe His Ser Lys Ile Pro Glu Phe Asn Lys
            180                 185                 190

Val Glu Cys Trp Gly Pro Leu Lys Asp Pro Ala Pro Pro Ser Ser Gly
        195                 200                 205

Leu Asp Gly Arg Pro Lys Ser Asp Glu Pro Met Trp Glu Leu Ser Arg
    210                 215                 220

Met Glu Arg Pro Lys Pro Cys Gln Glu Asp Cys Asn Cys Cys Phe Pro
225                 230                 235                 240

Thr Ile Pro Ser Ile Ser Trp Ser Pro Lys Asn Ser Glu Leu Glu Ser
                245                 250                 255

Thr
```